United States Patent [19]
Liu et al.

[11] Patent Number: 6,160,278
[45] Date of Patent: Dec. 12, 2000

[54] HYDROGEN-SENSITIVE PALLADIUM (PD) MEMBRANE/SEMICONDUCTOR SCHOTTKY DIODE SENSOR

[75] Inventors: Wen-Chau Liu; Huey-Ing Chen; Shiou-Ying Cheng, all of Tainan, Taiwan

[73] Assignee: National Science Council, Taipei, Taiwan

[21] Appl. No.: 09/321,535

[22] Filed: May 28, 1999

[30] Foreign Application Priority Data

Jun. 5, 1998 [TW] Taiwan ................................ 87108913

[51] Int. Cl.$^7$ .................................................. H01L 23/58
[52] U.S. Cl. ........................ 257/252; 257/253; 257/414; 257/472; 257/473; 257/485; 438/49; 204/431
[58] Field of Search .................................. 257/472, 473, 257/485, 453, 414, 253, 252; 438/580, 572, 573, 49; 204/431

[56] References Cited

U.S. PATENT DOCUMENTS

| | | | |
|---|---|---|---|
| 4,211,587 | 7/1980 | Massies et al. | 748/187 |
| 4,379,005 | 4/1983 | Hovel et al. | 148/187 |
| 4,543,442 | 9/1985 | Alcorn et al. | 136/255 |
| 5,516,725 | 5/1996 | Chang et al. | 437/177 |
| 5,652,443 | 7/1997 | Kasai | 257/252 |
| 5,923,072 | 7/1999 | Wada et al. | 257/473 |

FOREIGN PATENT DOCUMENTS

| | | |
|---|---|---|
| 356083717 | 7/1981 | Japan . |
| 356092524 | 7/1981 | Japan . |
| 357004143 | 1/1982 | Japan . |
| 402137370 | 5/1990 | Japan . |

OTHER PUBLICATIONS

Lundstrom et al, Journal of Applied Physics, vol. 46, No. 9, "A hydrogen-sensitive Pd-gate . . . ", Sep. 1975, pp. 3876–3881.

Steele et al, Applied Physics Letters, vol. 28, No. 11, "Palladium/cadmium-sulfide . . . ", Jun. 1, 1976, pp. 687–688.

K. Ito, Surface Science, vol. 86, "Hydrogen-sensitive Schottky barrier diodes", 1979, pp. 345–352.

(List continued on next page.)

*Primary Examiner*—William Mintel
*Attorney, Agent, or Firm*—Jacobson, Price, Holman & Stern, PLLC

[57] ABSTRACT

In this invention, a new, simple and small-size hydrogen-sensitive palladium (Pd) membrane/semiconductor Schottky diode sensor has been developed and fabricated. First, a high quality undoped GaAs buffer layer and an n-type GaAs epitaxial layer with the carrier concentration of $2 \times 10^{17}$ cm$^{313}$ is grown by molecular beam epitaxy (MBE) on a semi-insulated GaAs substrate. Then a thin Pd membrane is evaporated on the surface of the n-type GaAs epitaxial layer by the vacuum evaporation technique. It is well-known that palladium metal has excellent selectivity and sensitivity on hydrogen gas. When hydrogen gas diffuses to the Pd membrane surface, the hydrogen molecules will dissociate into hydrogen atoms. Some of the hydrogen atoms diffuse through the thin metal layer and form the palladium hydride near the metal-semiconductor interface. The hydride may effectively lower the work function of Pd metal. The lowering of work function results in the reduction of Schottky barrier height at the Pd metal-GaAs semiconductor interface and the modification in the measured current-voltage characteristics of the studied device. Experimental results reveal that, during the hydride formation process, the forward- and reverse-biased currents are increased by the increase of hydrogen concentration. It also demonstrates that the Schottky barrier height is indeed decreased with increasing the hydrogen concentration. Therefore, the studied device can be used in fabricating a high-performance hydrogen-sensitive sensor.

14 Claims, 5 Drawing Sheets

OTHER PUBLICATIONS

M. Armgarth et al, Appl. Phys. Lett., vol. 39, "A stable hydrogen–sensitive Pd gate . . . ", Jul. 1, 1981, pp. 91–92.

S. Morrison, Sensors and Actuators, vol. 2, "Semiconductor Gas Sensors", 1982, pp. 329–341.

A. Sibbald, IEE Proceedings, vol. 130, No. 5, "Chemical–sensitive field–effect . . . ", Oct. 1983, pp. 233–244.

Ching–Chang WEN et al, IEEE Trans. on Electron Devices, vol. 26, No. 12, "Gate–Controlled Diodes . . . ", Dec. 1979, pp. 1945–1951.

H. Wohltjen, Analytical Chemistry, vol. 56, No. 1, "Chemical Microsensors and . . . ", 1984, pp. 87A–88A.

HYDROGEN-SENSITIVE PALLADIUM (PD) MEMBRANE/SEMICONDUCTOR SCHOTTKY DIODE SENSOR

BACKGROUND OF THE INVENTION

1. Field of the Invention

The present invention demonstrates the structure of a new, simple and small-size hydrogen-sensitive palladium (Pd) membrane/semiconductor Schottky diode sensor and the method of fabricating it.

2. Description of the Prior Art

Recently gas sensors have been widely used in controlling the industrial process, prevention of the environmental pollution and medical diagnostics. People have paid attention to the detection of the concentration of the hydrogen gas and conducted research due to its danger of explosion. The series of sensors related to Pd membrane have attracted much attention among all kinds of hydrogen-sensitive sensors. The main reason is that palladium metal is an active catalyst. It will dissociate the hydrogen molecules on the Pd membrane surface into hydrogen atoms. Some of the hydrogen atoms diffuse through the palladium metal layer and adheres to the palladium metal-semiconductor or palladium metal-insulating layer interface. The palladium hydride may effectively lower the work function of Pd metal. The lowering of work function results in the modification of the measured current-voltage characteristics. I. Lundstrom et al. have proposed MOS field effect transistor with Pd gate on silicon substrate in *J. Appl. Phys.*, Vol. 46, pp. 3876 (1975). The sensor of this transistor structure is quite sensitive to hydrogen gas, but the difficulty in processing and the cost of which is high since the structure of transistor is more complicated and also need one layer of good quality $SiO_2$ insulating layer passivated on the top of the silicon substrate. Another simpler structure is to evaporate palladium metal on a semiconductor substrate to form a Schottky barrier. During the hydride formation process, the work function of Pd metal is lowered, which results in the reduction of Schottky barrier height to modify the output current characteristics of the studied device. Earlier Schottky diode hydrogen-sensitive sensor is fabricated by evaporating Pd metal on the substrate of II–VI semiconductor, e.g. the Pd—CdS structure reported by M. C. Steele et al. in *Appl. Phys. Lett.*, Vol. 28, pp. 687(1976) and the Pd—ZnO structure reported by K. Ito in *Surf. Sci.* Vol. 86, pp. 345. These Schottky diode devices can be used as for hydrogen-sensitive sensor. II–VI semiconductor substrate is used since the surface state density of IV and III–V semiconductor is higher so that the barrier height and the metal workfunction is not so closely related.

In this invention, a new hydrogen-sensitive Schottky diode sensor is proposed. The Schottky barrier is formed by evaporating palladium metal on the surface of III–V semiconductor (GaAs). To reduce the surface state density of the semiconductor, first, a high quality undoped GaAs buffer layer and an n-type GaAs epitaxial layer is grown by molecular beam epitaxy (MBE) on a semi-insulated GaAs substrate. Then a thin Pd membrane is evaporated on the surface of the n-type GaAs epitaxial layer by the vacuum evaporation technique of round metal mask. Since the surface state density of IV and III–V semiconductor is lowered, the work function of Pd metal will be lowered during the hydride formation process, which results in the reduction of Schottky barrier height to modify the output current characteristics of the studied device. Therefore the goal of hydrogen-sensitive sensor can be achieved. The present invention has the advantage of simple device structure & process, small size, so it has great potential in practical applications. Furthermore, the process technology of III–V semiconductor is far more sophisticated and stable than that of II–VI. Therefore, the sensor of the present invention can be combined with the other III–V components (e.g. high speed transistor, laser . . . ) to form excellent and versatile intelligent optoelectronic integrated sensor circuit.

SUMMARY OF THE INVENTION

In this invention, a new, simple and small-size hydrogen-sensitive palladium (Pd) membrane/semiconductor Schottky diode sensor, comprising: substrate, GaAs buffer layer, GaAs active layer, ohmic metal contact layer, Schottky metal contact layer is developed and fabricated.

Also, the present invention demonstrates that a high quality undoped GaAs buffer layer and an n-type GaAs epitaxial layer with the carrier concentration of $2\times10^{17}$ cm$^{-3}$ is grown by molecular beam epitaxy (MBE) on a semi-insulated GaAs substrate. Then a thin Pd membrane is evaporated on the surface of the n-type GaAs epitaxial layer by the vacuum evaporation technique.

The present invention demonstrates the structure of a new, simple and small-size hydrogen-sensitive palladium (Pd) membrane/semiconductor Schottky diode sensor. Please refer to the attached figures and detailed description of the present invention for further understanding the special feature and the contents of the technology of the present invention. However, the attached figures are for reference only, but not for confining the scope of the present invention.

The deviation of Schottky barrier height=[the voltage without hydrogen gas]-[the voltage with hydrogen gas]

Figure 4:
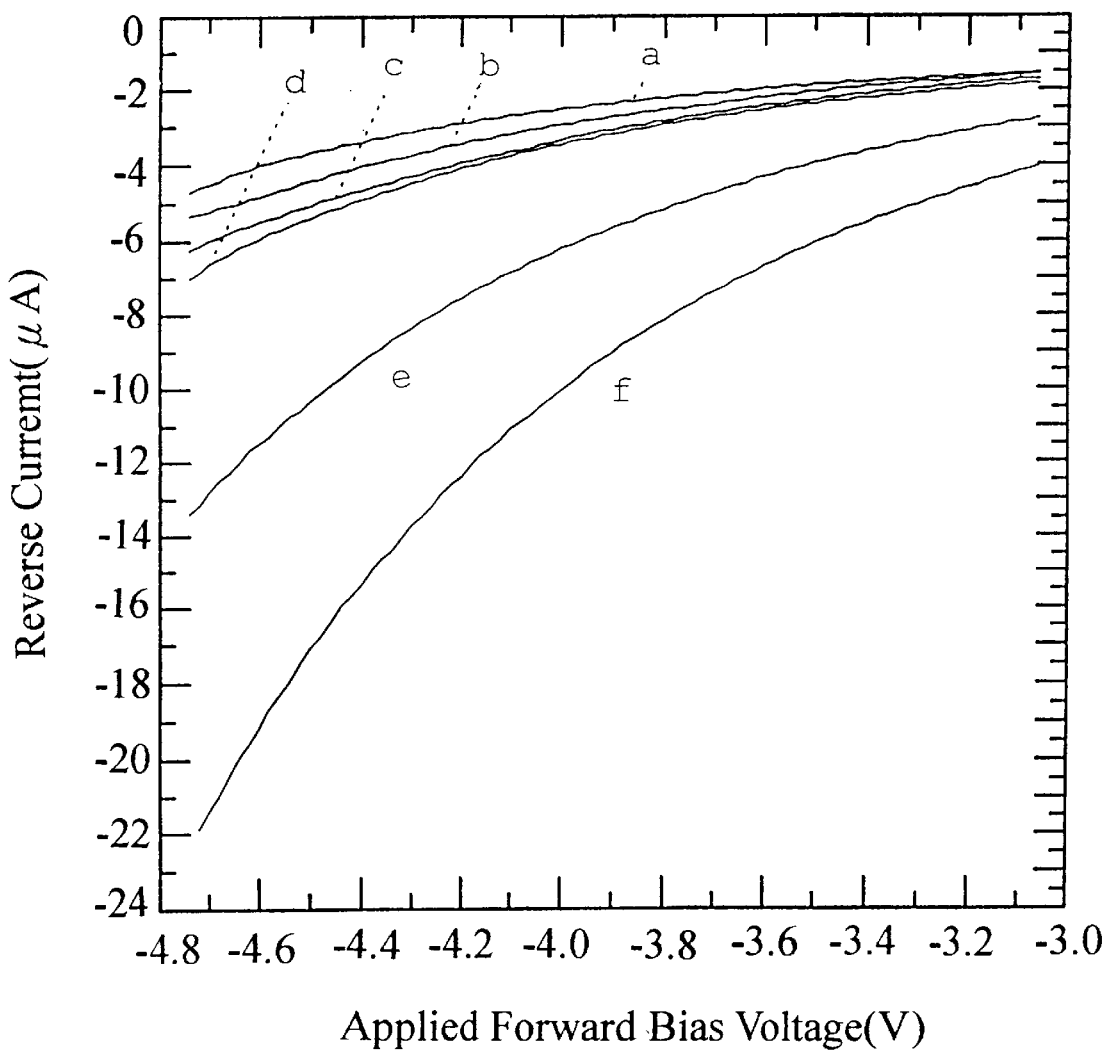

FIG. 4. The reverse biased current-voltage characteristics of the present invention as a function of hydrogen concentration. a . . . air b . . . $H_2$=1% c . . . $H_2$=2% d . . . $H_2$=3% e . . . $H_2$=4% f . . . $H_2$=5%

Figure 5:
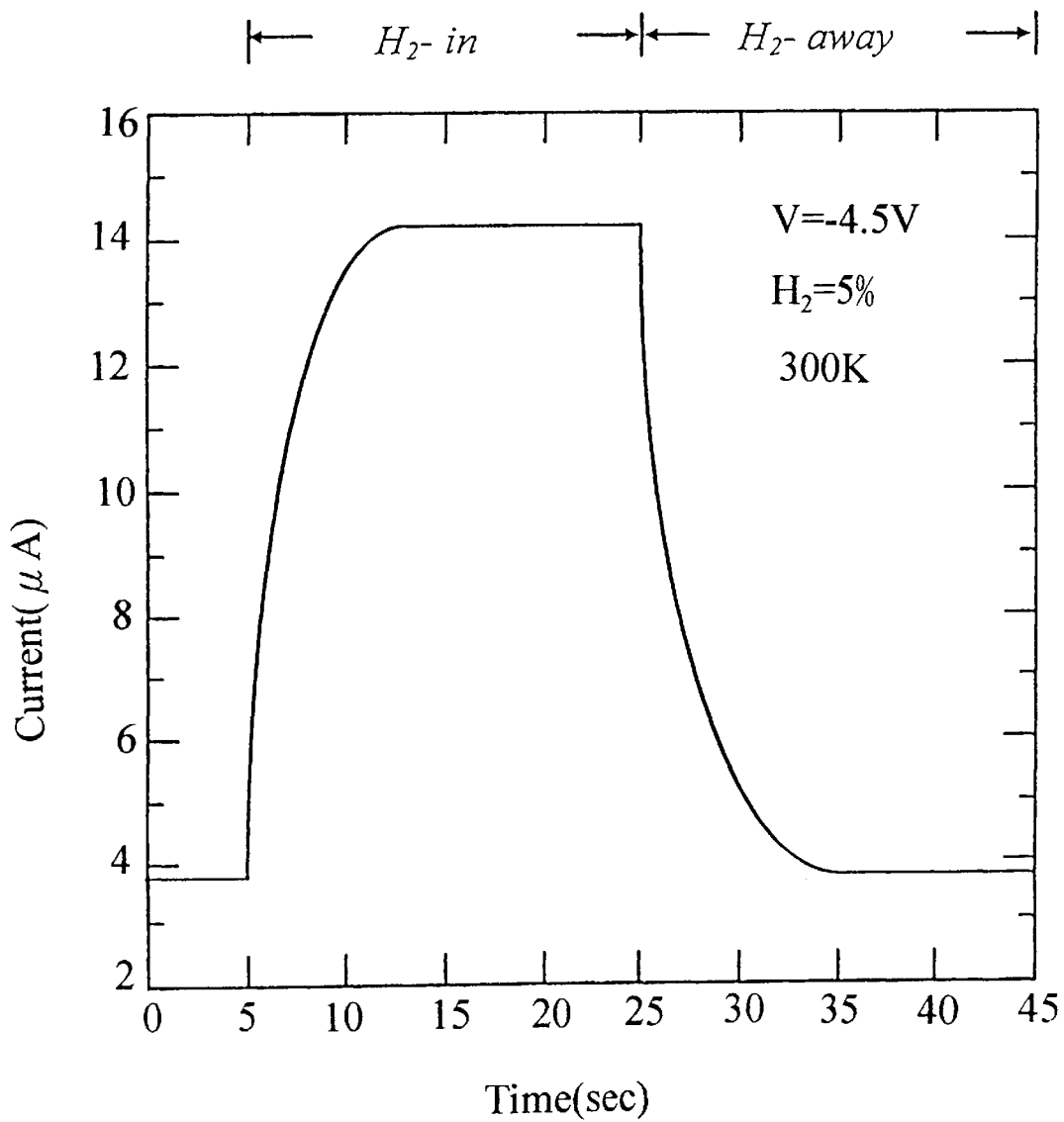

FIG. 5. The current response with time during the hydrogen formation process.

DESCRIPTION OF THE PREFERRED EMBODIMENTS

The present invention demonstrates the structure of a new, simple and small-size hydrogen-sensitive palladium (Pd) membrane/semiconductor Schottky diode sensor, comprising: substrate, GaAs buffer layer, GaAs active layer, ohmic metal contact layer, Schottky metal contact layer. The substrate is semi-insulating GaAs, the GaAs buffer layer is i-GaAs with 0.5~5 µm thickness and is undoped, the GaAs active layer is n-GaAs with 0.1~2 µm thickness, n=1× $10^{17}$~$3\times10^{18}$ cm$^{-3}$, the ohmic metal contact layer is Au—Ge (88%/12%) alloy with 3000–5000 Å thickness, the Schottky metal contact layer is Pd with 2000–5000 Å thickness.

First, a high quality undoped GaAs buffer layer and an n-type GaAs epitaxial layer with the carrier concentration of $2 \times 10^{17}$ cm$^{-3}$ is grown by molecular beam epitaxy (MBE) on a semi-insulated GaAs substrate. Then a thin Pd membrane is evaporated on the surface of the n-type GaAs epitaxial layer by the vacuum evaporation technique. Since palladium metal has excellent selectivity and sensitivity on hydrogen gas. When hydrogen gas diffuses to the Pd membrane surface, the hydrogen molecules will dissociate into hydrogen atoms. Some of the hydrogen atoms diffuse through the thin metal layer and form the palladium hydride near the metal-semiconductor interface. The hydride may effectively lower the work function of Pd metal. The lowering of work function results in the reduction of Schottky barrier height at Pd (metal)-GaAs, (semiconductor) interface and the modification in the measured current-voltage characteristics of the studied device. Experimental results reveal that, during the hydride formation process, the forward- and reverse-biased currents are increased by the increase of hydrogen concentration. It also demonstrates that the Schottky barrier height is indeed decreased with increasing the hydrogen concentration. Therefore, the studied device can be used in fabricating a high-performance hydrogen-sensitive sensor.

Figure 1:
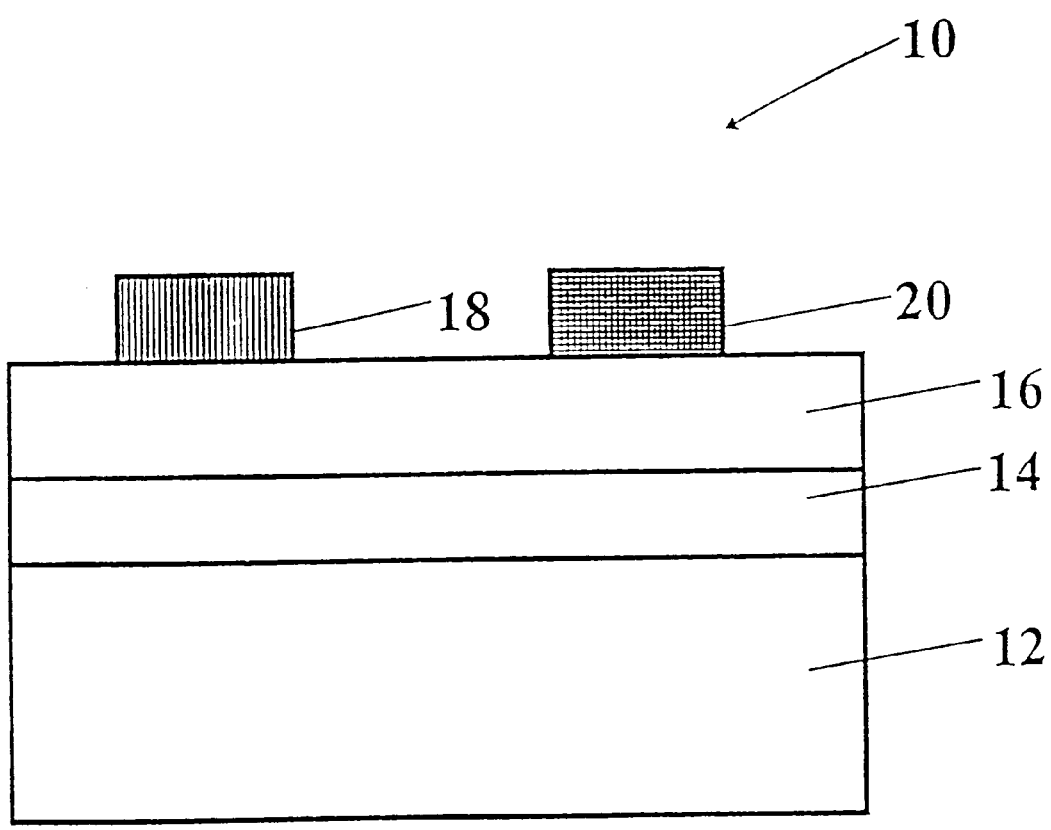
FIG. 1 The structure of a hydrogen-sensitive palladium (Pd) membrane/semiconductor Schottky diode sensor of the present invention.

FIG. 1 is one of the embodiments of hydrogen-sensitive palladium (Pd) membrane/semiconductor Schottky diode sensor (10) of the present invention. The structure is as follows (downward): semi-insulating GaAs substrate (12), undoped GaAs buffer layer with 1 μm thickness (14), GaAs active layer with 2 μm thickness, n=$2 \times 10^{17}$ cm$^{-3}$ (16), Au—Ge ohmic metal contact layer (18) with 5,000 Å thickness, Pd membrane Schottky metal contact layer with 2,000 Å thickness(20).

Figure 2:
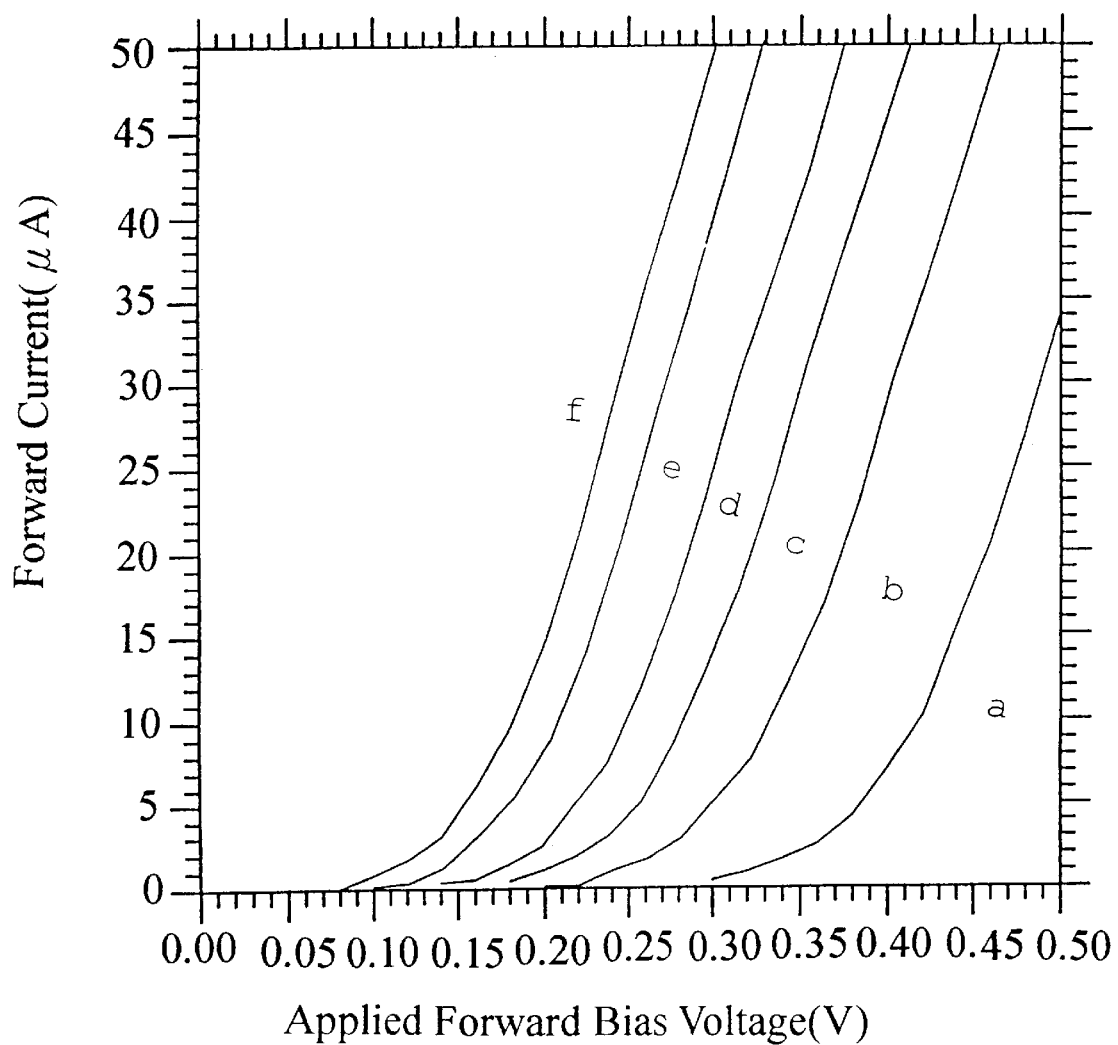
FIG. 2 The forward biased current-voltage characteristics of the present invention as a function of hydrogen concentration. a . . . air b . . . $H_2$=1% c . . . $H_2$=2% d . . . $H_2$=3% e . . . $H_2$=4% f . . . $H_2$=5%

FIG. 2 is the forward biased current-voltage characteristics of the present invention during the hydrogen formation process. As shown in the figure, the conducting voltage decreases with the increase of the hydrogen concentration in the testing ambient. i.e. The curve shifts to the origin with the increase of the hydrogen concentration.

Figure 3:
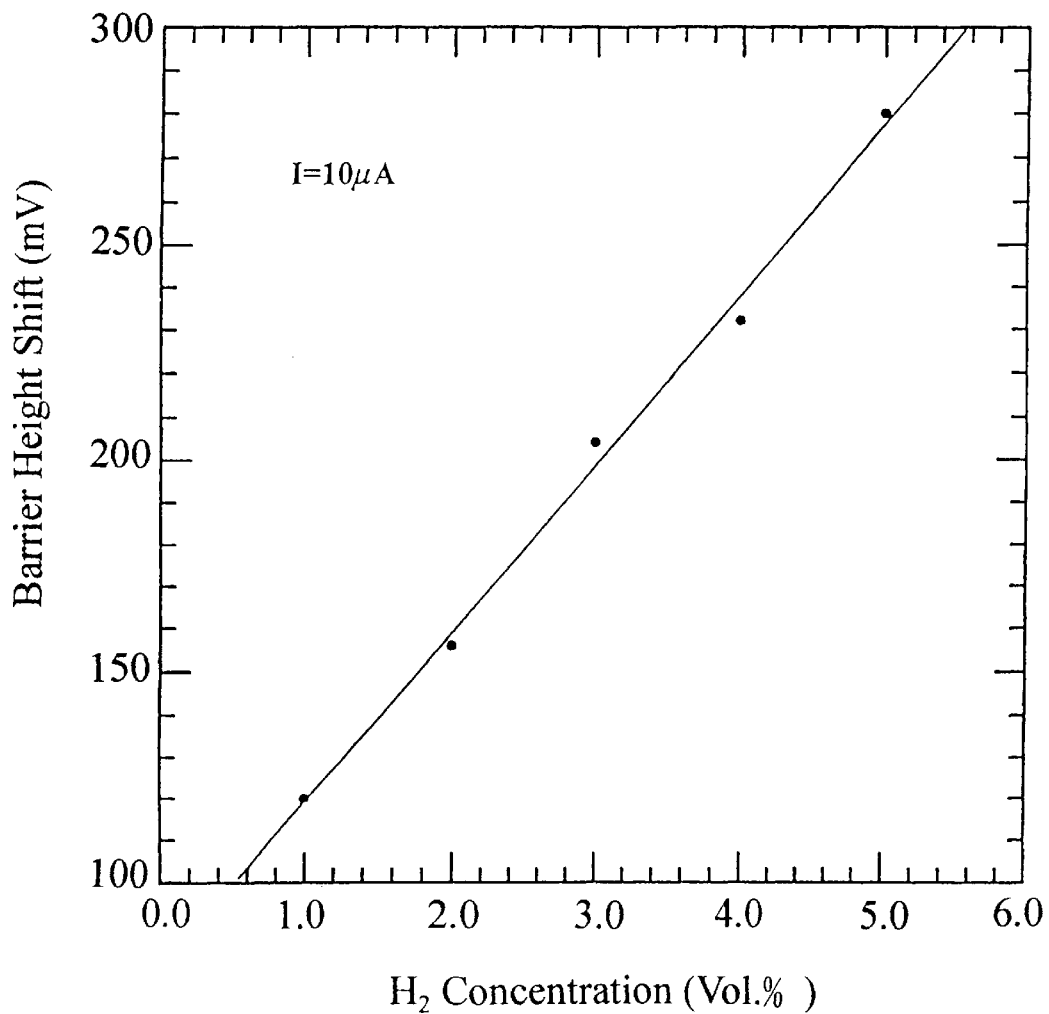
FIG. 3 The influence of the hydrogen concentration on the Schottky barrier height at a constant forward current of 10 µA.

FIG. 3 is the shift of Schottky barrier height (i.e. the deviation of Schottky barrier height=the voltage without hydrogen gas–the voltage with hydrogen gas) with the hydrogen concentration in the testing ambient when forward biased and current held constant at 10 μA. As shown in the figure, the amount of the reduction of Schottky barrier height increases with the increase of the hydrogen concentration. Therefore, the Schottky barrier height at the metal-semiconductor interface is indeed lowered after introducing the hydrogen gas.

FIG. 4 is the reverse biased current-voltage characteristics of the present invention during the hydrogen formation process. Obviously, the current increases with the increase of the hydrogen concentration, especially when the external reverse bias is larger. This also demonstrates that the increase of the hydrogen concentration is indeed helpful to lower Schottky barrier height of this device.

FIG. 5 is the current response with time during the hydrogen formation process. During the measurement, the reverse bias is held at −4V, the concentration of hydrogen is 5%, the testing temperature is room temperature (300K). As shown in the figure, introducing hydrogen gas will increase the current, the rise time of the current waveform is less than 8 sec. When hydrogen gas is cut off, the falling time of the current waveform is less than 15 sec.

From the above, the sensor device of the present invention is indeed very sensitive to the ambient hydrogen concentration. And the response time is very short in the testing environment at room temperature; the characteristics is much better than other sensors which can only response fast in the high temperature environment. Furthermore, since the minimum limitation of hydrogen gas explosion is several percent, so the hydrogen-sensitive sensor of the present invention is indeed in the scope of practical usage.

What is claimed is:

1. A hydrogen-sensitive palladium (Pd) membrane/semiconductor Schottky diode sensor, comprising:
    a substrate for forming said hydrogen-sensitive palladium (Pd) membrane/semiconductor Schottky diode sensor,
    a GaAs buffer layer next to said substrate for forming said sensor,
    a GaAs active layer for forming said sensor and positioned next to said GaAs buffer layer away from said substrate,
    an ohmic metal contact layer for forming said sensor and positioned next to said GaAs active layer away from said GaAs buffer layer and said sensor, and
    a Schottky metal contact layer for forming said sensor and positioned next to said GaAs active layer away from said GaAs buffer layer and said substrate.

2. The hydrogen-sensitive palladium (Pd) membrane/semiconductor Schottky diode sensor according to claim 1, wherein said substrate is semi-insulating GaAs.

3. The hydrogen-sensitive palladium (Pd) membrane/semiconductor Schottky diode sensor according to claim 1, wherein said buffer layer is i-GaAs.

4. The hydrogen-sensitive palladium (Pd) membrane/semiconductor Schottky diode sensor according to claim 1, wherein said active layer is n-GaAs.

5. The hydrogen-sensitive palladium (Pd) membrane/semiconductor Schottky diode sensor according to claim 1, wherein said ohmic metal contact layer is Au—Ge (88%/12%) alloy.

6. The hydrogen-sensitive palladium (Pd) membrane/semiconductor Schottky diode sensor according to claim 1, wherein said Schottky metal contact layer is Pd.

7. The hydrogen-sensitive palladium (Pd) membrane/semiconductor Schottky diode sensor according to claim 3, wherein said buffer layer is 1 μm thick and undoped.

8. The hydrogen-sensitive palladium (Pd) membrane/semiconductor Schottky diode sensor according to claim 4, wherein said active layer is 2 μm thick, n=$2 \times 10^{17}$ cm$^{-3}$.

9. The hydrogen-sensitive palladium (Pd) membrane/semiconductor Schottky diode sensor according to claim 5, wherein said ohmic metal contact layer is 5000 Åthick.

10. The hydrogen-sensitive palladium (Pd) membrane/semiconductor Schottky diode sensor according to claim 6, wherein said Schottky metal contact layer is 2000 Åthick.

11. The hydrogen-sensitive palladium (Pd) membrane/semiconductor Schottky diode sensor according to claim 3, wherein said buffer layer is 0.5~5 μm thick and undoped.

12. The hydrogen-sensitive palladium (Pd) membrane/semiconductor Schottky diode sensor of claim 4, wherein said active layer is 0.1~2 μm thick, n=$1 \times 10^{17}$~$3 \times 10^{18}$ cm$^{-3}$.

13. The hydrogen-sensitive palladium (Pd) membrane/semiconductor Schottky diode sensor of claim 5, wherein said ohmic metal contact layer is 3000–5000 Åthick.

14. The hydrogen-sensitive palladium (Pd) membrane/semiconductor Schottky diode sensor according to claim 6, wherein said Schottky metal contact layer is 2000–5000 Åthick.

* * * * *